United States Patent [19]

Gear

[11] 4,103,229

[45] Jul. 25, 1978

[54] CONTINUOUS-FLOW, RESISTIVE-PARTICLE COUNTING APPARATUS

[75] Inventor: Adrian R. L. Gear, Charlottesville, Va.

[73] Assignee: The University of Virginia, Charlottesville, Va.

[21] Appl. No.: 763,630

[22] Filed: Jan. 28, 1977

[51] Int. Cl.² ............................................. G01N 27/00
[52] U.S. Cl. ............................. 324/71 CP; 73/432 PS
[58] Field of Search ......................... 324/71 CP, 71 R; 73/432 PS

[56] References Cited

U.S. PATENT DOCUMENTS

| | | | |
|---|---|---|---|
| 3,810,010 | 5/1974 | Thom | 324/71 CP |
| 3,871,770 | 3/1975 | Von Behrens et al. | 324/71 CP X |
| 3,902,115 | 8/1975 | Hogg et al. | 324/71 CP |
| 3,941,479 | 3/1976 | Whitehead | 324/71 CP X |
| 3,973,196 | 8/1976 | Hogg | 324/71 CP |

OTHER PUBLICATIONS

"Improving Resolution in Coulter Counting by Hydrodynamic Focusing" by L. Spielman & S. L. Goren, *Journal of Colloid and Interface Science*, 26, 175-182 [1968].

Primary Examiner—Rudolph V. Rolinec
Assistant Examiner—Vincent J. Sunderdick
Attorney, Agent, or Firm—Oblon, Fisher, Spivak, McClelland & Maier

[57] ABSTRACT

Apparatus for continuous-flow resistive-particle counting includes an injection jet directed at a counting or sensing orifice, particle-containing electrolyte being pumped through the jet in an amount which is in excess of the volume flow rate normally passing through the sensing orifice. The orifice therefore only detects and analyzes the particles contained in the injected solution and not in the bulk electrolyte disposed within the external vessel. Internal and external electrodes are respectively disposed upon opposite sides of the orifice, that is, within the sensing orifice tube and within the external vessel and the electrical connection between the electrodes is maintained at all times. Performance in measuring erythrocyte and platelet numbers and size is very comparable to that of static, resistive-particle counting. The apparatus further includes a simple overflow, fluidically connected to the external vessel, which serves as a drain for the excessively pumped solution, and the injection jet is vertically and pivotably adjustable so as to properly orient the same with respect to the sensing orifice.

4 Claims, 6 Drawing Figures

FIG. 3a INITIAL BACKGROUND: 16 COUNTS

FIG. 3b PUMPING ERYTHROCYTES: 22,742 COUNTS

FIG. 3c STATIC ERYTHROCYTES: 22,244 COUNTS

FIG. 4

CONTINUOUS-FLOW, RESISTIVE-PARTICLE COUNTING APPARATUS

The invention described herein was made in the course of work under a grant or award from the Department of Health, Education and Welfare and also partly funded by the Virginia Heart Association and thereby may be manufactured and used by or for the Government for governmental purposes without the payment of any royalties thereon or therefore.

BACKGROUND OF THE INVENTION

1. Field of the Invention

The present invention relates generally to resistive-particle counting and more particularly to the field of automated particle enumeration and sizing.

2. Description of the Prior Art

Particle-size distribution and concentration are important properties of countless powdered, slurried, or emulsified materials as well as of biological cells, fluid contaminants, and foodstuffs. In processes involving particulate materials, particle size is a critical factor in dynamic process control, equipment evaluation, product quality control, and research and investigation. Present methods of particle-size measurement include microscope counting sieving, adsorption and permeability, and a number of Stokesian methods. Although most of these methods have been automated to varying degrees in recent years with significant improvements in speed and accuracy, there is still a need for instrumentation to reduce frequently inherent tedium, time delay, and error.

One other well-known approach is the optical sensing zone method wherein the passage of a particle through a light beam enables particle numbers to be easily determined, however, the same provides information very difficult to relate in a meaningful way to particle size or shape. By combining the same with continuous-flow techniques, successful techniques have been in clinical use for nearly 10 years, however, disadvantages nevertheless remain. In order to accomplish platelet counting, lysing agents must be used in order to remove the massive interference which would otherwise be caused by erythrocytes. For example, ammonium oxalate, in combination with a detergent, has been previously used, as has 2 M urea to lyse erythrocytes. A small disadvantage with such techniques, however, is that white cells are counted along with the platelets and have to be determined independently for a subsequent correction.

A major alternative to the optical sensing-zone methods is resistive particle counting which has been a valuable analytical technique for the industrial, medical, and scientific communities for approximately 20 years, and which has provided information on particle numbers and particle size with respect to particles ranging in size from approximately 0.4–10 $\mu$ or more in diameter. The more sophisticated apparatus have in fact been a considerable advance over earlier technology, providing up to seven parameters of clinical interest, mainly with regard to erythrocytes and white cells. In particular, clinical laboratories all over the world carry out enormous numbers of routine measurements of erythrocytes, white cells and blood platelets. Particle volumes are determined too, but this usually requires more time and expensive apparatus and is often not needed for medical diagnostic purposes. The advent of minicomputers has helped automate data reduction and has been very useful for calculating mean particle volumes and giving other statistical information from population histograms.

The major advantage of such apparatus is inherent in the original concepts where electrical information is available for determining both particle numbers and size, and potentially for shape too, with pulse-width analysis. The latter two parameters are of course not presently available with optical measuring systems. Other advantages are that pulse-height analysis is readily performed, and economical minicomputers provide capabilities of extensive data manipulation, aside from exhibiting great speed.

There are, however, several disadvantages of resistive counting. Simple clogging of the sensing orifice has been perhaps the major problem with all counters of such type, and one particular type of apparatus attempts to rectify such a problem through the provision of three orifice tubes each for white cells and erythrocytes, that is, six in all, with a corresponding duplication of circuitry. Comparison of the various data values from each then provides a means of detecting orifice blockage, however, the net result is complex and extremely expensive apparatus, which of course detracts from the inherent simplicity and ease of resistive-counter operation. Other approaches to the problem have also been utilized, such as, for example, a simple backflush plunger which is very valuable for cleaning nearly all blockages, or the specific timing of the orifice flow rate has been another effective way to detect such problems. Still further, special redesign of the aperture tube, as disclosed in U.S. Pat. No. 3,746,976 to Hogg, wherein two orifices are used to minimize eddy currents, and therefore the generated electronic signals, has allegedly resulted in a self-cleaning orifice.

Other problems, however, have included poor resolution and skewed distributions of particles. The latter problem was apparently resolved, for example, with respect to erythrocytes, wherein the provision of longer orifice path lengths gave superior distributions. Several recent approaches to the question of resolution demonstrate that it is often necessary to make complex modifications to the orifices. For example, Thom, as disclosed in U.S. Pat. No. 3,810,010, has designed a clever combination of two orifices, instead of one, wherein the particles are sucked out of the first orifice and surrounded by a sheath of particle-free electrolyte prior to their entry into the second and sensing orifice. The improved resolution stems from the original concept of hydrodynamic focusing, however, Thom's apparatus is quite complex, and is dependent upon skilled glass-blowing and very precise geometries. In addition, due to the suction of the particles into the orifice together with the sheath of particle-free diluent, accurate counts of the detected particles are not obtained.

In U.S. Pat. No. 3,793,587 to Thom and Schulz, the apparatus disclosed therein serves to distinguish leucocytes from erythrocyte agglomerates, and to distinguish between two particles of equal volume but different shape. These goals are achieved by the use of two coaxial orifices of different path lengths, and a feed tube directed to the first orifice. As in U.S. Pat. No. 3,810,010, however, the same requires hydrodynamic sucking, which is a critical feature for success of the invention, and which, as noted hereinabove, draws in a quantity of particle-free diluent around the sucked particles through the first orifice. Consequently, the first orifice does not detect the true concentration of particles in the particle suspension.

Still further, a major disadvantage still remains in that intermittent and manual presentation of samples is still required. That is, individual liquid samples have to be handled and positioned over the sensing orifice prior to each analysis. In addition, relatively-large quantities of blood (1.3 ml) have to aspirate into the machine, mainly to flush away previous samples, and after appropriate dilution, the sample is subject to a static count. On the other hand, flow-counting techniques do have an inherent advantage over the static resistive approach in that they are more flexible in that multiple samples are able to be run in a continuous train towards the sensing zone. In addition, specific manipulations, such as reagent addition, are readily performed on the samples before analysis. Nevertheless, further improvement and/or refinement of such apparatus, and the techniques associated therewith is desired.

SUMMARY OF THE INVENTION

Accordingly, it is an object of the present invention to provide a new and improved resistive-particle counting apparatus.

Another object of the present invention is to provide a new and improved resistive-particle counting apparatus of the continuous-flow type.

Still another object of the present invention is to provide a new and improved continuous-flow resistive-particle counting apparatus which is able to measure properties of particles previously unattainable with conventional resistive techniques or apparatus.

Yet another object of the present invention is to provide a new and improved continuous-flow resistive-particle counting apparatus which is able to analyze a plurality of different samples presented in a sequential manner to the injection jet.

Still yet another object of the present invention is to provide a new and improved continuous-flow resistive-particle counting apparatus which is able to measure the rate and extent of various particle reactions, such as, for example, blood-platelet aggregation, platelet interaction with bacteria, and erythrocyte fragility.

A further object of the present invention is to provide a new and improved continuous-flow resistive-particle counting apparatus which is able to analyze any number of samples without physical manipulations of the same within the vicinity of the sensing zone orifice.

A yet further object of the present invention is to provide a new and improved continuous-flow resistive-particle counting apparatus which is able to measure particle size, as well as absolute numbers, of a large number of samples, such as, for example, the quantitating and sizing of erythrocytes or blood platelets, directly.

The foregoing and other objects are achieved in accordance with the present invention through the provision of an apparatus for continuous-flow resistive-particle counting which includes an injection jet directed at a counting or sensing orifice, particle-containing electrolyte being pumped through the jet in an amount which is in excess of the volume flow rate normally passing through the sensing orifice. The orifice therefore only detects and analyzes the particles contained in the injected solution and not in the bulk electrolyte disposed within the external vessel. Internal and external electrodes are respectively disposed upon opposite sides of the orifice, that is, within the sensing orifice tube and within the external vessel and the electrical connection between the electrodes is maintained at all times. Performance in measuring erythrocyte and platelet numbers and size is very comparable to that of static, resistive-particle counting. The apparatus further includes a simple overflow, fluidically connected to the external vessel, which serves as a drain for the excessively pumped solution, and the injection jet is vertically and pivotably adjustable so as to properly orient the same with respect to the sensing orifice.

BRIEF DESCRIPTION OF THE DRAWINGS

Various other objects, features, and attendant advantages of the present invention will be more fully appreciated as the same becomes better understood from the following detailed description when considered in connection with the accompanying drawings, in which like reference characters designate like or corresponding parts throughout the several views, and wherein.

DETAILED DESCRIPTION OF A PREFERRED EMBODIMENT

Figure 1:
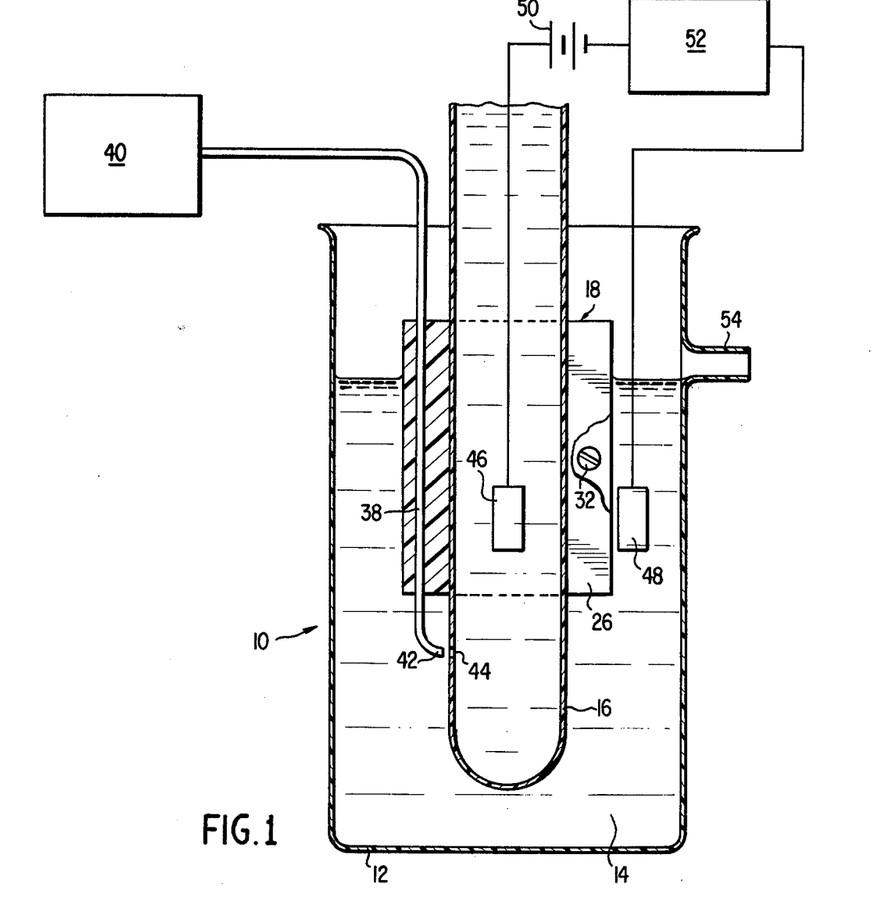
FIG. 1 is a schematic view, in a vertical plane, of a continuous-flow resistive-particle counting apparatus constructed in accordance with the present invention and showing its cooperative parts.
Figure 2:
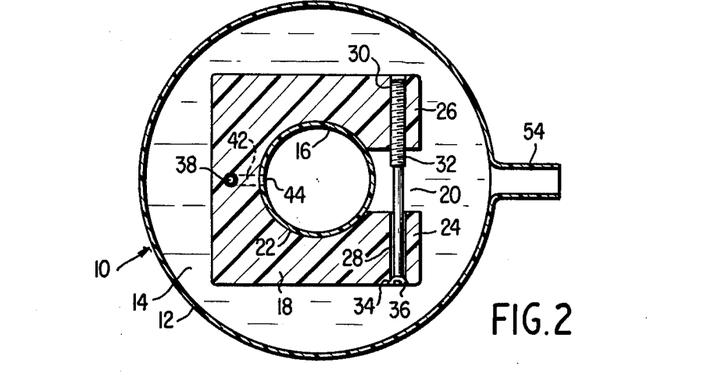
FIG. 2 is a schematic view, in a horizontal plane, of the apparatus of FIG. 1.

Referring now to the drawings, and more particularly to FIGS. 1 and 2 thereof, the continuous-flow, resistive-particle counting apparatus of the present invention is generally indicated by the reference character 10 and is seen to include a container or beaker 12 within which is disposed a bulk electrolyte 14. An orifice tube 16, which has the general configuration of a conventional test tube, is centrally disposed within a supporting block 18 so as to be coaxially disposed therewith. The block 18 has substantially the configuration of a rectangular parallelepiped, with a longitudinal opening 20 defined within one side thereof serving to define an open area which renders the block C-shaped in horizontal cross-section, as best seen in FIG. 2, the block therefore also having a cylindrical opening 22 within which orifice tube 16 is disposed.

Block 18 may be fabricated of Lucite and the arms or legs 24 and 26 of block 18, which serve to define opening 20, are respectively provided with aligned openings or bores 28 and 30 within which a suitable fastening member, such as, for example, a bolt 32, may be disposed. Bore 28 of block leg 24 is non-threaded and the outer end 34 thereof has a conical configuration which matingly engages the head 36 of bolt 32, while bore 30 is threaded so as to threadedly engage the threaded end portion of bolt 32. An injection tube 38, which may be fabricated of stainless steel (20 gauge), is fixedly embedded, along a longitudinal portion thereof, within block 18 so as to extend substantially parallel to orifice tube 16. The upstream end of tube 38 is fluidically connected to a pumping system, generally indicated by the reference character 40, while the downstream end of tube 38 projects below block 18 and is curved radially inwardly with, for example, a 2 mm radius of curvature, so as to define an injection jet 42.

Orifice tube 16 is provided with a sensing orifice 44 within a sidewall portion thereof, and the jet 42 is of course disposed within the vicinity of, and oriented towards, orifice 44, with the end of tube 38 disposed approximately 1 mm from orifice 44. Still further, as a result of the provision of fastener 32, and the selective loosening or tightening of the same, block 18 may be moved vertically, or pivoted about the longitudinal axis thereof, relative to orifice tube 16 so as to selectively accurately position jet 42 relative to orifice 44. It has been determined that the injection tube 38, and more particularly jet 42, does not have to be disposed directly in front of sensing orifice 44, and such relative disposition provides the useful capability of direct unhindered viewing of the orifice, for the important and routine checking of orifice cleanliness or blockages, by means of conventional microscope systems built into commercial conventional resistive particle counters.

As can also be appreciated from FIG. 1, a first electrode 46 is fixedly disposed within orifice tube 16 so as to be coaxial therewith, while a second electrode 48 is fixedly disposed within container 12 within the vicinity of, or adjacent to, block 18 and at a vertical level corresponding to that of electrode 46. The electrodes are of course disposed within an electrical circuit which includes a power source 50 and suitable, conventional particle measuring, detecting, and displaying apparatus generally indicated by the reference character 52. Container 12 is further provided with an overflow conduit 54 which is fluidically connected to a waste container, not shown, for accumulating the excessively pumped or waste bulk electrolyte. The pumping system may comprise any number or combinations of syringe pumps or even relatively-pulseless peristaltic pumps. Appropriate valves or connections are needed to link these pumps with the inlet tube 38.

The continuous flow apparatus described hereinabove can be adapted to conventional orifices of any commercial resistive particle counter. The counter was combined with a PDP-8M minicomputer, DEC tape, and an oscilloscope for purposes of automatic data collection and reduction. For most of the work with platelets and erythrocytes, a 48 $\mu$ orifice was used, although a 30 $\mu$ may be employed. Two 60 ml plastic, disposable syringes, disposed in parallel, were utilized in the pumping system and the tubing (0.8 mm I.D.; 1.6 mm O.D.) and connectors were made of Teflon.

Good counting performance with blood cells is obtained by cell dilution with 0.15 M NaCl (0.9% w/v). The syringes in the syringe pump are then filled with this solution. The saline routinely used should be filtered twice through 0.45 $\mu$ filters so as to render the same essentially particle free, and 50–200 $\mu$l of packed erythrocytes diluted to 1 liter of electrolyte was used as the standard particle suspension. A flow rate of 10 ml/min was found to be about optimal with the 20-G injection needle 38, however, runs with a smaller 23-G needle showed about 5 ml/min to be sufficient, although the smaller needle was more sensitive to poor positioning near the sensing orifice 44.

Routine counting is made simpler and faster by using the timers built into most commercial counters or in computer-controlled systems. Thus counts are usually made for time periods of 10 seconds and repeated four to five times for each experimental situation. A flow-rate determination for the given orifice then allows a simple conversion of particle counts to counts per unit volume. With a 48 $\mu$ orifice, the following counter settings were employed: for erythrocytes: current = $\frac{1}{2}$, gain = 8$\frac{1}{2}$, and log = 6; for platelets: current = $\frac{1}{2}$, gain = 48, and log = 4.

With respect to the operating principles of the present invention, the number and size of particles in an electrically conductive liquid are determined by the application of the well-known resistance principle. This principle consists of sucking the suspension to flow through orifice 44. As each particle passes through the orifice, it replaces its own volume of electrolyte within the orifice, momentarily changing the resistance value between the electrodes 46 and 48. This change produces a voltage pulse of short duration having a magnitude proportional to particle volume, and the resultant series of pulses is electronically processed by apparatus 52.

Voltage-pulse height is proportional to amplifier gain, aperture current, and resistance change due to the particle passage ($\Delta E = G \times I \times \Delta R$). Expressing the particle in its electrical effect as a right cylinder aligned with the orifice axis, it can be shown that the change in aperture resistance caused by a particle is:

$$\Delta R = \frac{\rho o v}{A^2} \times \left( \frac{1}{1 - \frac{\rho o}{\rho}} - \frac{a}{A} \right)^{-1}$$

wherein:
$\rho o$ = electrolyte resistivity,
$A$ = aperture area normal to axis,
$v$ = particle volume
$\rho$ = effective particle resistivity, and
$a$ = area normal to aperture axis of equivalent right cylinder for particle as oriented in passage.

In other words, current fluctuations are obtained which are approximately proportional to the volume of the particles upon the passage of the particles through the measuring opening. In carrying out this process, a potential difference is set up between the two electrodes 46 and 48 disposed in the electrolytic test liquid 14 on both sides of the measuring orifice 44, so as to cause a certain current to flow through the electrolyte liquid from one electrode to the other electrode through the measuring orifice. With a constant potential difference between the two electrodes, this current intensity changes upon the passage of a particle through the measuring orifice due to the fact that the conductivity of a particle is different from the conductivity of the electrolytic surrounding the particle. Thus, basically, a certain electrical resistance is measured between the two electrodes which resistance changes when a particle is disposed in the measuring orifice. This resistance is of course dependent on the type of electrolyte employed and on the type, size and number of the particles suspended in this electrolyte.

If the potential difference between the two electrodes is increased, the current through the electrolyte also increases linearly unless the conductivity of the electrolyte is changed by the heat produced by the existence of a stronger current. In an analogous manner a constant measuring current can be set between the two electrodes whereupon the passage of a particle through the measuring opening causes a change in the electrical potential difference between the electrodes.

Corresponding to the increase in current in the electrolyte, the current differences in the measuring circuit caused by the passage of a particle through the measuring opening also increase. If latex particles are added to the electrolyte, for example, it can be noted that the changes in current increase linearly with the current in the measuring circuit.

If the ratio of current changes to the current in the measuring circuit is evaluated, the absolute resistivity of the measuring circuit, i.e., of the electrolyte path in the measuring circuit, is no longer incorporated in the measurement. Influences from increases in temperature of the electrolyte are also eliminated by utilizing such a ratio in measuring the particles. Consequently, it is the relative change of the resistivity of the electrolyte path in the measuring opening that is evaluated.

Electrical grounding of various segments of the apparatus has been deemed necessary, as failure to ground may result in spurious signals being detected and amplified, particularly as the waste electrolyte is conducted out of the overflow passage 54 to the large waste container, not shown, disposed below the counter. The following simple ground leads and precautions have therefore proven effective in eliminating electrical interference:

a. The injection tube 38 leading from the syringe pump apparatus 40, the waste container, not shown, as well as the waste overflow tube 54 are all shielded with aluminum wrapping;

b. The inlet shield of the aluminum foil is grounded to both the outlet shield and the resistive-particle counter chassis;

c. The outlet tube shield is grounded to the waste container shield; and d. The 3-way, metal stopcock, not shown, at the end of the syringe is also grounded to the counter chassis.

In accordance with the present invention, the basic principle is to inject the solution containing the particles directly at the sensing-zone orifice 44. In this manner the orifice detects, or "sees", only those particles in the stream, and is totally unresponsive to the composition of the bulk medium in the container surrounding the orifice tube. The direction of the jet of liquid directly at the orifice has the effect of "focusing", or aligning the particles before they enter the orifice. This improves their resolution, or distribution width at half-maximal height of a particle population distribution.

With respect to the influence of the rate of injection on the particle counts and size, Table 1 shows how the observed particle counts and their size are influenced by changing the rate of injection at the sensing-zone orifice 44. It may be seen that between flow rates of approximately 35 to 11 ml per minute, the number of particle pulses remains almost constant and close to the theoretical control value of 100% in the static or non-flowing situation. At the fastest speed tested, 46.2 ml per minute, some 15% more counts than the control were detected. These excess counts probably arise from turbulence caused by the high rate of injection at the sensing orifice 44. The larger standard deviations of 12 to 15% compared with about 1 to 2% at the lower flow rates or in static counting, also suggest a lack of stability at the very highest injection rates. Finally, the particle size was significantly below the control value of 40.5 $\mu_3$ for the rat erythrocytes used in the experiment.

The data in Table 1 reveal that very slow injection rates failed to give the correct number of particles and size, although the influence of size, or really pulse height, was not as severe as at the highest injection rates. Such experiments demonstrate that the flow system is capable of injecting particles at the sensing orifice with detection characteristics in good agreement with the classical or non-flowing situation, and for the 20 G needle used, flow rates between 23.1 and 11.6 ml per minute gave optimal results.

TABLE 1

| Injection Rate (ml per min) | Particle Counts (% non-flowing control) | Log Mean Volume ($\mu^3$) |
|---|---|---|
| 46.2 | 115.3 ± 14.6 | 33.0 ± 0.9 |
| 34.7 | 100.7 ± 12.2 | 36.6 ± 0.5 |
| 23.1 | 103.7 ± 1.8 | 40.2 ± 0.0 |
| 17.3 | 101.6 ± 1.3 | 40.2 ± 0.0 |
| 11.6 | 102.0 ± 1.0 | 40.5 ± 0.1 |
| 5.78 | 89.8 ± 3.3 | 41.6 ± 0.8 |
| 2.89 | 83.5 ± 1.7 | 41.9 ± 0.6 |
| 0, (Control) | 100.0 ± 0.9 | 40.5 ± 0.9 |

Effect of Injection Flow Rate on Particle Counts and Size

The large syringe pump was filled with rat erythrocytes (40 $\mu$l of packed cells diluted to 1 liter in 0.15 M NaCl) and then the injection flow rate through the 20 G needle was varied to determine its influence on the observed particle counts and size. A minimum of six, 10-second analyses were carried out at each flow rate, and the mean and standard deviations are shown.

Another inportant consideration of the flow system is to know the speed of response in detecting particle numbers and their size immediately after starting up the syringe pump. This was tested in the following way. Dilute rat erythrocytes (40 $\mu$l packed cells to 1 liter of saline) were used to fill the injection syringe and tubing right up to the point of injection. The beaker 12 with overflow 54 was then thoroughly rinsed with particle-free saline and consequently, 10-second background analyses initiated. Following each 10 second accumulation, the minicomputer automatically calculates and prints out the total number of particles and their log mean, mode and median size. This process requires about 7 seconds, and during the 5th print-out the syringe pump was started.

The results given in Table 2 represent the direct Teletype output and reveal the low initial background of some 10 counts per 10 seconds, followed by immediate detection of the injected erythrocytes. The very first data accumulation on starting the pump gave normal detection of both particle numbers and size. This observation is important in that it proves that the sensing zone orifice 44 responds only to that solution in its immediate vicinity. The bulk electrolyte in the overflow beaker 12 (some 10 ml) was initially free of any particles, and thus has no effect on the ability to detect successfully particles in the stream injected at the orifice.

The response time of the system is therefore less than 7 seconds (the computer calculation time between consecutive analyses). Only at injection rates slower than 6 ml per minute did the response time become greater than 7 seconds; or, in other words, the first 10-second data accumulation was not equal to subsequent ones.

TABLE 2

| Condition | Particle Numbers (per 10 sec) | Volume ($\mu^3$) | | |
|---|---|---|---|---|
| | | Log Mean | Log Mode | Log Median |
| Background | 5 | Not meaningful, All below 2.5 $\mu^3$ | | |
| | 8 | | | |
| | 9 | | | |
| | 9 | | | |
| Pump Started → | 16 | | | |
| | 22,742 | 43.1 | 46.1 | 43.1 |
| | 22,271 | 40.2 | 46.1 | 43.1 |
| Erythrocytes Pumping | 22,420 | 40.2 | 43.1 | 43.1 |
| | 22,391 | 40.2 | 46.1 | 43.1 |
| | 22,759 | 40.2 | 46.1 | 43.1 |
| Control, Non-Pumping | 22,076 ± 109 (n = 6) | 40.8 | 45.1 | 45.1 |

Response Time of the Flow System

The injection system was first filled with diluted rat erythrocytes (40 $\mu l$ packed cells to 1 liter in saline). Repetitive 10-second background counts were then made and after five of these automatic ounts, the syringe pump was started (Flow Rate was 11.6 ml/min).

Figure 3A:
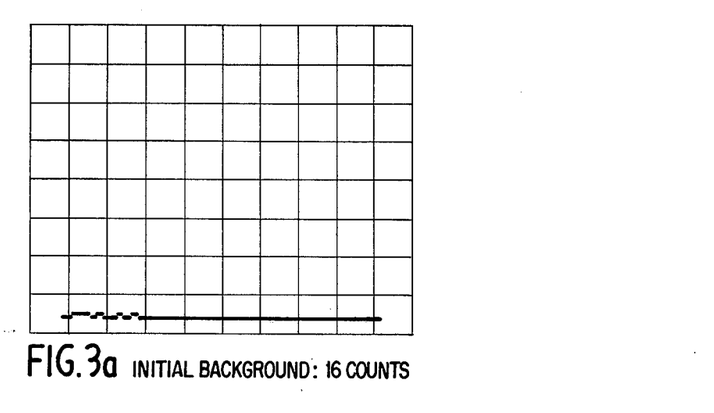
FIGS. 3a–3c are photographs of oscilloscope displays of particle distributions corresponding respectively to an initial background, a first data accumulation upon injecting rat erythrocytes at the sensing orifice, and a static or non-pumping distribution of the same concentration of erythrocytes, respectively.
Figure 3B:
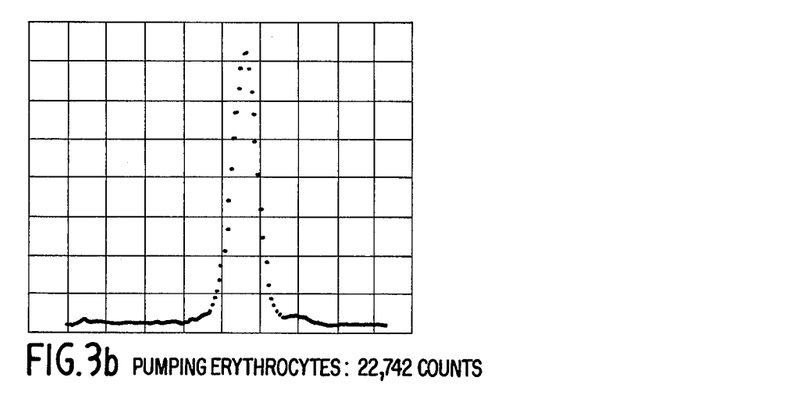
Figure 3C:
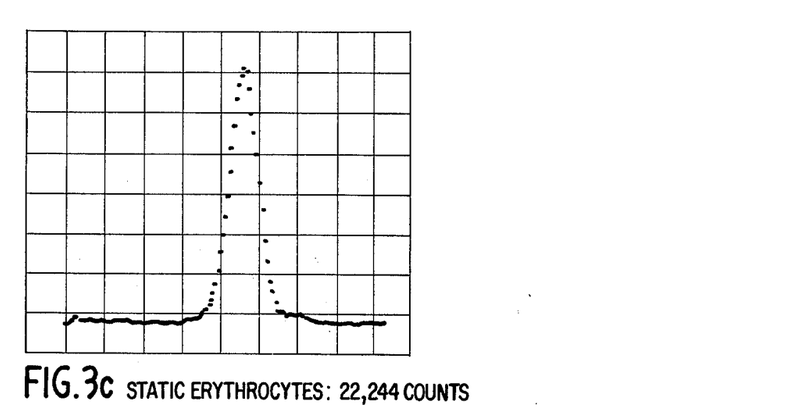

A more dramatic way to demonstrate the response time of the system is illustrated in FIGS. 3a–3c which are three photographs of the oscilloscope distribution for the non-flowing background immediately before switching on the syringe pump (3a), the very next data accumulation of pumped erythrocytes (3b), and one representative control, or non-pumping analysis (3c). The ordinate gives particle numbers and the axis is proportioned to size with 128 channels being represented. Total particle counts are indicated below each figure.

Figure 4:
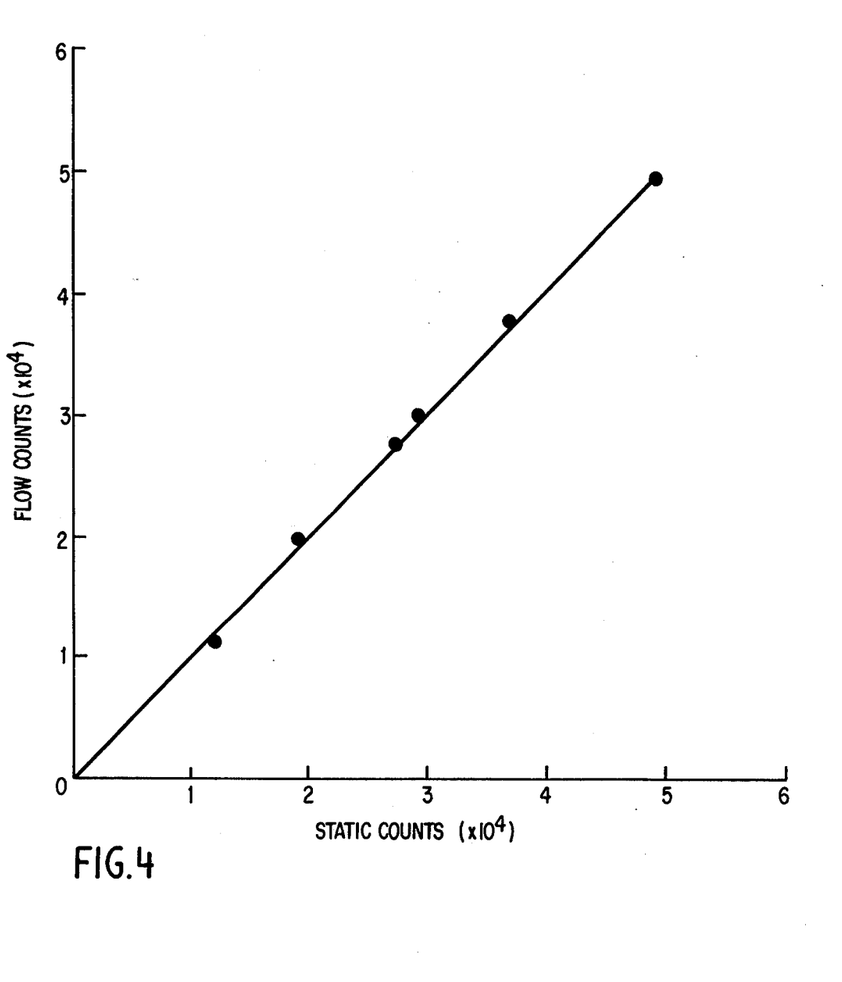
FIG. 4 is a graphical plot comparing particle counts derived in accordance with the continuous-flow resistive-particle counting apparatus of the present invention, as well as those derived by the static or classical method of resistive-particle counting.

The data noted hereinabove reveal that the injection flow system has a fast response time (less than 7 seconds) and gives particle numbers and volumes which agree well with results from non-flowing techniques (Table 1). For better comparison between the two procedures, six separate experiments on different preparations of erythrocytes were carried out, and FIG. 4 is a simple plot of the numbers of particles counter per 10 seconds for the continuous-flow system versus those obtained by the static, or classical method of resistive particle counting. The six erythrocyte preparations were analysed on different days and varied about 4-fold in concentration. The slope of 0.9994 with a correlation coefficient of 0.9988 and an intercept of only − 72 out of 50,000 total counts per 10 seconds, indicates that flow counting gives results virtually identical to static counting.

Not shown in FIG. 4 are the standard deviations, which were too small to be indicated accurately. The individual points represent the means for between five to 12 consecutive counts on the same particle preparation. Averaging the standard deviations for static counting gave 277 ± 140 counts per 10 seconds. The corresponding value for flow counting was 601 ± 403, with the mean of the gross counts being 29,169 for static and 29,258 per 10 seconds for flow counting. This result indicates that flow counting almost doubles the standard deviation seen in static counting. The reason for this may lie in extra turbulence near the sensing zone orifice, as suggested by the data obtained at different flow rates (Table 1).

Most interest in resistive-particle counting lies in the simple desire to know particle numbers. This is the easiest and cheapest parameter to obtain. However, for some applications it is useful to know particle size; for example disorders of erythrocyte or blood platelets are often characterized by abnormal particle volumes. For this reason it was important to determine whether flow counting gives the same particle volumes as the static procedure. The data in Table 3 compare the two techniques for human erythrocytes and platelets as well as for rat erythrocytes. There was no significant size difference for either type of erythrocytes. However, the human platelets subjected to continuous flow counting were significantly smaller, if only slightly so $p<0.01$ using the paired Student's $t$ test), being 6.28 $\mu^3$ versus 6.54 $\mu^3$ for static counting. The reason for this could be that flow through about 100 cm of the 0.8 mm teflon tubing causes some platelet fragmentation.

TABLE 3

Comparison of Particle Volumes Measured by Continuous-Flow, or Static Counting

The syringe pump was filled with human erythrocytes, platelets or rat erythrocytes, appropriately diluted in 0.15 M NaCl. Particle size (log mean volume, $\mu^3$) was measured at a flow rate of 11.6 ml per min. The syringe pump was then stopped and volumes measured under static, or non-flowing conditions. The $p$ value for comparing the two counting situations is from Students $t$ test for paired samples. The number of particle preparations from different individuals is given in brackets, and standard deviations are also indicated.

TABLE 3

| | Mean Particle Volume ($\mu^3$) | | |
|---|---|---|---|
| | Human | | Rat |
| Condition | Platelets | Erythrocytes | Erythrocytes |
| Static | 6.54 ± 1.47 | 88.4 ± 13.4 | 48.6 ± 7.8 |
| Flowing | 6.28 ± 1.45 | 89.0 ± 12.0 | 49.1 ± 9.9 |
| p | <0.01 (9) | >0.1 (6) | >0.1 (3) |

The foregoing results demonstrate that the new procedure of continuous-flow counting of the present invention preforms essentially as well as the classical or static method of resistive-particle counting. This was true with respect to both particle numbers and the size of blood platelets or erythrocytes. It has also been shown that adequate electrical grounding is important, and that either execssively high or excessively low rates of injection at the sensing orifice could cause slight errors in particle numbers and size.

The main aspect which facilitates the sucessful operation of the apparatus of the present invention is that an open electrical contact exists at all times between the internal and external electrodes 46 and 48 and the sensing orifice only detects or "sees" the particles in the stream of the injected electrolyte. This was demonstrated most clearly in Table 2 where the very first data accumulation on starting the syringe pump detected 22,742 erythrocytes, a value close to the control or non-pumping situation. At this stage the bulk electrolyte surrounding the injected stream was completely free of particles and after one 10-sec data analysis plus 7 sec for computer calculation, was only about 33% exchanged with the excess of the injected particle-containing electrolyte. For the standard 48 $\mu$ orifice, 0.27 ml per minute of the injected particles passed through orifice 44 while at the same time 11.6 ml were actually injected. Therefore, approximately 97.7% of the injected stream enters the bulk electrolyte in the surrounding beaker and only 2.3% actually traverses the sensing orifice for analysis.

The above observation that less than 3% of the ejected flow enters the orifice pertains only to the specific combination of a 20 Gauge tube 38 directed at the standard 48 μ orifice 44. Other experiments with a 23 Gauge tube showed that the injection rate could be decreased by about one-half without a loss of counts. This fact strongly suggests that the actual velocity of nozzle injection, and not just the overall flow rate, is important for determining the fidelity of subsequent detection by the sensing orifice. Here flow rates of the order to 10 m per sec are common. Future development of flow counting would certainly be profitable in terms of optimizing the nozzle geometry and ejection velocity for raising the low ratio of sensing volume to injected volume. It should be mentioned though that the present system is extremely simple, easy to construct, and performance is not critically dependent upon very precise nozzle positioning.

It is thus seen that several major improvements and potential uses are effected and rendered feasible by continuous-flow counting. It is additionally noted that the present invention provides the capability of analyzing multiple samples without the necessity of sample handling near the sensing zone orifice. The results presented here, especially those in Table 2, suggest that it would be feasible to send a train of different samples down the inlet tube to the sensing orifice 44, each sample being separated from each other by means of a blank or "spacer" of particle-free electrolyte. This procedure would be similar to that used in a number of existing clinical autoanalysers, except that these often have an air bubble separating the samples. Bubbles however, are undesirable in resistive-particle counters since they lead to erratic or spurious counts. It may be possible to remove the same before final injection at the sensing orifice, however, such techniques of bubble removal require special handling and it is therefore felt that the simple inclusion of particle-free "spacers" is the best initial way to approach the problem of multiple sampling.

A dual-channel syringe pump may be used, of which one syringe will be filled with an appropriate dilution of packed erythrocytes in isotonic saline, while the other one is filled with particle-free saline. Manual operation of a valve will direct either particles or blank solution down the inlet tube. Preliminary experience of the flow-counting techniques has shown that the response time is less than 7 seconds for full detection of absolute numbers or size from an initial blank.

The computer software is able to be modified so as to measure such sequential counts more simply and rapidly. This capability should prove valuable for helping determine the most suitable combinations of sample and spacer volumes, or the times for given injection flow rates. It should be possible to have a spacer corresponding to 5 seconds, or less, and a sample of about 10 seconds, such that potential counting rates could be at least 1 every 15 seconds. In this regard it might be mentioned that the software can accept variable analyses and await commands such that it is possible to synchronize the print-out of particle numbers with each new sample.

With respect to ways of introducing the multiple samples to the inlet tube, one potential way will be to employ a peristaltic-type pump which is essentially pulseless. The LKB pumps are among the closest in this regard. Consequently, a 5-channel LKB pump may be compared with the ideal, and pulseless, Harvard syringe pumps normally used, and over a typical, 10-second analysis time by the resistive counter, slight pulsations, which could induce varying count rates, can be averaged out to a steady mean value. One of the channels will then serve as a blank channel, and the other to deliver sample. By employing suitable by-pass valves, it is possible to deliver either sample or blank down the common inlet tube to the injection point.

A second potential way to conduct multiple sampling is to use an infusion-withdrawal, or reciprocating syringe pump. While one syringe is filling with new sample, the other can be injecting blank spacer into the inlet tube to the resistive counter. The advantages of pulseless pumping are retained with this approach. It should be possible to have the counter commence analyzing, immediately after the momentary interruption of flow as one syringe stops and the other starts pumping, by means of the variable analysis and await times programmed into the software mentioned earlier.

With respect to the above, standard tests will be performed to check for: (a) linearity of response to serial dilution of sample, (b) carryover of one sample to the next, or in other words, the effectiveness of the blank spacers, (c) the influence of different injection flow rates together with spacer and sample volumes, and (d) the ability to determine mean particle size as well as the routine particle numbers.

It is thus seen that a primary commercial value of the invention would be in the routine analysis of blood-cell constituents in hospital, clinical laboratories. The continuous-flow principle of the present invention would allow for multiple samples to be analysed, each separated by a "spacer" of particle-free electrolyte. Appropriate lytic agents could be added, if necessary, and using the threshold discriminators build into most commercial instruments, the same can allow for multiple cell-type analysis, for example, red cells, white cells and platelets.

In accordance with well-known principles, the voltage pulses reflective of the counted particles are amplified and fed to a threshold circuit having an adjustable screen-out voltage level, and if this level is reached or exceeded by a pulse, the pulse is registered. Thus, each count represents the number of particles larger than the selected threshold-size level in a given volume of suspension. By taking a series of counts at various threshold settings, data are directly obtained for plotting cumulative particle frequency or concentration versus particle volume (or mass, given constant density).

Other potential uses of the apparatus of the present invention reside in following particle-particle interactions. The reaction of platelets with bacteria has already been studied by the author under a static counting situation, and it should be quite convenient to determine actual rates by flow counting. Also interaction of bacteria with leucocytes and Rickettsiae with erythrocytes are additional examples where preliminary investigations with the resistive counter suggest feasibility for flow counting. A final indication of potential use is in determining the osmotic fragility of erythrocytes, knowledge of which is useful clinically. Measurement has not been previously possible with resistive-particle counters and early experiments indicate this to be simpler and much quicker than the present centrifugation and optical test.

Platelet-bacteria interaction is not as well-known as the platelet function in blood clotting. However, it may be a significant line of defense against bacterial infection, with the platelets possibly immobilizing bacteria for later destruction by leucocytes. Some information exists on various features of this particle-particle interaction, mainly from electron-microscopy and aggregometry studies. However, little is known about the efficiency of the process and what basic metabolic changes occur.

It is proposed to employ the apparatus outlined above to investigate the efficiency and characteristics of the platelet-bacteria interaction. Initial experiments may involve putting *E.coli* in the syringe normally used for the aggregating agent. Some preliminary batch-counting experiments have demonstrated that resistive techniques are well suited for monitoring the platelet-bacteria interaction. Subsequently, work with other strains of bacteria can be accomplished.

A new technique has also been developed in the laboratory whereby the resistive-particle counter apparatus can directly measure the precentage of erythrocytes that lyse after a certain osmotic stress, results of osmotic lysis tests being of great diagnostic value in certain hematological conditions.

The apparatus thus provides the ability to use whole blood to measure erythrocytes, platelets as well as white cells. Previous techniques for resistive counters will be used where a lysing agent removes interference of erythrocytes for counting white cells. The former are counted independently after an additional dilution; platelets on the other hand must be counted separately and need special handling.

2M urea can be used as an erythrocyte lytic agent for counting platelets from whole blood. The counter of the present invention has an automatic normalizer which corrects for any change in electrolyte conductivity. This feature is particularly valuable for accurate sizing. It is likely though that platelet sizes may be abnormal due to exposure to the hypertonic 2M urea, and this point should be checked against routine platelet sizing in isotonic saline.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. Continuous-flow resistive-particle counting apparatus comprising:
    container means for housing a bulk electrolyte;
    an orifice tube closed at the lower end thereof and having a sensing orifice defined within a side wall portion thereof, a portion of said electrolyte thereby being disposed within said tube;
    a first electrode disposed within said electrolyte disposed within said orifice tube;
    a second electrode disposed within said bulk electrolyte disposed within said container;
    electric circuit means including a power source, electrically connecting said first and second electrodes;
    fluid pumping means having a down-stream tube equipped with an injection jet, said down-stream tube disposed within the electrolyte in said container at a position radially outwardly of said orifice tube and within the vicinity of said sensing orifice of said orifice tube for forcefully injecting a fluid jet of said particles to be counted toward said sensing orifice at a flow rate which is at least tenfold the normal flow rate of said electrolyte from said container through said sensing orifice into said orifice tube; and
    means disposed within said electrical circuit for counting said particles passing through said sensing orifice.

2. Continuous-flow resistive-particle counting apparatus as set forth in claim 1, further comprising:
    a holding block disposed about said orifice tube and having a selectively variable diameter so as to selectively grasp or release said orifice tube and thereby render said block selectively fixed about said tube, or vertically movable or pivotable about the longitudinal axis of said tube, respectively;
    means for controlling the diameter of said block; and
    said injection means includes an injection jet tube fixedly disposed within said block, said injecting tube having an injection jet defined within the end thereof disposed within said vicinity of said sensing orifice,
    whereby the disposition of said injection jet relative to said sensing orifice is adjustable.

3. Continuous-flow resistive-particle counting apparatus as set forth in claim 2, wherein:
    said block is substantially C-shaped in horizontal cross-section; and
    said means for controlling the diameter of said block is a threaded fastener threadedly engaged within the arms of said block defining said C-shaped portion thereof.

4. Continuous-flow resistive-particle counting apparatus, as set forth in claim 1, further comprising:
    overflow means defined within said bulk electrolyte container.

* * * * *